US005755829A

United States Patent [19]

Terranova et al.

[11] Patent Number: 5,755,829

[45] Date of Patent: May 26, 1998

[54] PROCESSES FOR DYEING KERATINOUS FIBERS WITH COMPOSITIONS WHICH CONTAIN N-SUBSTITUTED 4-HYDROXYINDOLINE DERIVATIVES AS COUPLERS AND OXIDATION BASES

[75] Inventors: Eric Terranova, Asnieres; Aziz Fadli, Le Blanc Mesnil; Alain Lagrange, Coupvray, all of France

[73] Assignee: L'Oreal, Paris, France

[21] Appl. No.: 761,756

[22] Filed: Dec. 5, 1996

[30] Foreign Application Priority Data

Dec. 6, 1995 [FR] France .................................. 95 14372

[51] Int. Cl.[6] ...................................................... A61K 7/13

[52] U.S. Cl. .......................... 8/409; 8/407; 8/408; 8/423; 8/574

[58] Field of Search ............................... 8/406, 407, 408, 8/409, 410, 423, 574; 548/490, 491

[56] References Cited

U.S. PATENT DOCUMENTS

| | | | |
|---|---|---|---|
| 3,649,160 | 3/1972 | Kalopissis et al. | 8/409 |
| 5,427,588 | 6/1995 | Lagrange et al. | 8/423 |

FOREIGN PATENT DOCUMENTS

| | | |
|---|---|---|
| A-285179 | 10/1988 | European Pat. Off. . |
| A-604278 | 6/1994 | European Pat. Off. . |
| A-2008797 | 1/1970 | France . |

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

The subject of the invention is a composition for the oxidation dyeing of keratinous fibers containing at least one N-substituted 4-hydroxyindoline derivative as coupler and at least one oxidation base. The invention also relates to new N-substituted 4-hydroxyindoline derivatives, to their process of synthesis, to their use as couplers for the oxidation dyeing of keratinous fibers, in combination with at least one oxidation base, and to the dyeing processes in which they are used.

26 Claims, No Drawings

PROCESSES FOR DYEING KERATINOUS FIBERS WITH COMPOSITIONS WHICH CONTAIN N-SUBSTITUTED 4-HYDROXYINDOLINE DERIVATIVES AS COUPLERS AND OXIDATION BASES

The present invention relates to a composition for the oxidation dyeing of keratinous fibres and in particular of human keratinous fibres, such as hair, containing at least one N-substituted 4-hydroxyindoline derivative as coupler, and at least one oxidation base.

It is known to dye keratinous fibres and in particular human hair with dyeing compositions containing oxidation dye precursors, in particular ortho- or para-phenylenediamines, ortho- or para-aminophenols or heterocyclic compounds, generally called oxidation bases. Oxidation dye precursors, or oxidation bases, are colourless or slightly coloured compounds which, in combination with oxidizing products, can give rise, by an oxidative coupling process, to coloured and colouring compounds.

It is also known that it is possible to vary the shades obtained with these oxidation bases by combining them with couplers or colouring modifiers, the latter being selected in particular from aromatic meta-diamines, meta-aminophenols, meta-diphenols and some heterocyclic compounds, such as indoline compounds.

The variety of the molecules involved as oxidation bases and couplers make it possible to obtain a rich palette of colours.

The colouring obtained by virtue of these oxidation dyes is "permanent" and must, moreover, satisfy a certain number of requirements. Thus, it must be without disadvantage from a toxicological viewpoint, it must make it possible to obtain shades within the desired intensity and it must behave well in the face of external agents, such as light, bad weather, washing, permanent wave, perspiration or friction.

The dyes must also make it possible to cover white hair. Finally, the dyes must be as non-selective as possible, i.e., they must make it possible to obtain differences in colouring which are as slight as possible along the same keratinous fibre, which may, in fact, be sensitized (i.e., damaged) to a varying extent between its tip and its root.

Compositions for the oxidation dyeing of keratinous fibres containing, as couplers, at least one indoline derivative and in particular at least one 4-hydroxyindoline derivative which can be N-substituted by a $C_1$–$C_4$ alkyl radical, have already been proposed, in particular in French Patent Application FR-A-2,008,797. Such compositions make it possible to achieve varied ranges of shades but they are not, however, entirely satisfactory. In particular, they are not satisfactory from the viewpoint of the behaviour of the colourings obtained with respect to various attacks to which hair may be subjected and in particular with respect to light and shampoos.

The inventors have now discovered that it is possible to obtain powerful new dyes which possess little selectivity, which are particularly resistant and which are capable of generating intense colourings within varied shades by using specific 4-hydroxyindoline derivatives, namely suitably N-substituted derivatives. These compounds, which are partly novel in themselves, are, moreover, easy to synthesize.

This discovery forms the basis of the present invention.

A subject of the invention is therefore a composition for dyeing keratinous fibres and in particular human keratinous fibres such as hair, characterized in that it comprises, in a medium appropriate for dyeing:

as coupler, at least one N-substituted 4-hydroxyindoline derivative of formula (I) and/or at least one acid addition salt thereof:

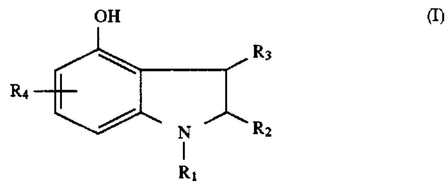

(I)

in which:

$R_1$ represents a ($C_1$–$C_4$) monohydroxyalkyl radical; a ($C_2$–$C_4$) polyhydroxyalkyl radical; a ($C_1$–$C_4$)alkoxy($C_1$–$C_4$)alkyl radical; a hydroxy($C_1$–$C_4$)alkoxy($C_1$–$C_4$)alkyl radical; an acetyl or ($C_1$–$C_4$) aminoalkyl radical; a ($C_1$–$C_4$) aminoalkyl radical in which the amine is mono- or disubstituted by a ($C_1$–$C_4$) alkyl group, by an acetyl group, by a ($C_1$–$C_4$) monohydroxyalkyl group or by a ($C_2$–$C_4$) polyhydroxyalkyl group; a ($C_1$–$C_4$) alkylthio($C_1$–$C_4$)alkyl radical or a monohydroxy ($C_1$–$C_4$)alkylthio($C_1$–$C_4$)alkyl radical; a polyhydroxy ($C_2$–$C_4$)alkylthio($C_1$–$C_4$)alkyl radical; a ($C_1$–$C_4$) carboxyalkyl radical; a ($C_1$–$C_4$)alkoxycarbonyl ($C_1$–$C_4$)alkyl radical or a acetylamino($C_1$–$C_4$)alkyl radical; a ($C_1$–$C_4$) cyanoalkyl radical; a ($C_1$–$C_4$) trifluoroalkyl radical; a ($C_1$–$C_4$) haloalkyl radical; a ($C_1$–$C_4$) phosphoalkyl radical or a ($C_1$–$C_4$) sulphoalkyl radical;

$R_2$ and $R_3$, which are identical or different, represent a hydrogen or halogen atom; a ($C_1$–$C_4$) alkyl radical; a carboxyl radical; a ($C_1$–$C_4$)alkoxycarbonyl radical or a formyl radical;

$R_4$ represents a hydrogen or halogen atom; a ($C_1$–$C_4$) alkyl radical; a ($C_1$–$C_4$) alkoxy radical; an acetylamino radical; a ($C_1$–$C_5$) monohydroxyalkyl radical; a ($C_2$–$C_4$) polyhydroxyalkyl radical; a ($C_1$–$C_4$)alkoxy ($C_1$–$C_4$)alkyl radical; a thiophene radical, a furan radical; a phenyl radical; a ($C_1$–$C_4$) aralkyl radical; a phenyl or ($C_1$–$C_4$) aralkyl radical substituted by a halogen atom, a ($C_1$–$C_4$) alkyl, a trifluoromethyl, a ($C_1$–$C_4$) alkoxy or an amino or by an amino mono- or disubstituted by a ($C_1$–$C_4$) alkyl radical; a ($C_1$–$C_4$) alkylamino($C_1$–$C_4$)alkyl radical or a di($C_1$–$C_4$) alkylamino($C_1$–$C_4$)alkyl radical;

and at least one oxidation base.

In the formula (I) above, the ($C_1$–$C_4$) alkyl and ($C_1$–$C_4$) alkoxy groups can be linear or branched and, among the halogen atoms, mention preferably may be made of chlorine, bromine, iodine and fluorine.

The couplers of formula (I) in accordance with the invention are distinguished from the known products of the abovementioned document FR-A-2,008,797 essentially by the nature of the substituent $R_1$ in the 1-N position.

Preferably, according to the present invention, the substituent $R_1$ is selected from the $C_1$–$C_4$ monohydroxyalkyl radicals and the $C_2$–$C_4$ polyhydroxyalkyl radicals.

The colourings obtained with the dyeing composition according to the invention are varied and powerful shades which show little selectivity and exhibit excellent properties of resistance simultaneously with respect to atmospheric agents, such as light and bad weather, and with respect to perspiration and various treatments to which hair may be subjected e.g., shampoos or permanent deformations. These properties are particularly noteworthy especially with respect to light and shampoos.

Mention may preferably be made, among the N-substituted 4-hydroxyindoline derivatives of formula (I) which can be used as couplers in the compositions according to the invention, of:

4-hydroxy-1-N-(β-hydroxyethyl)indoline, 4-hydroxy-1-N-(β-hydroxypropyl)indoline, 1-N-acetyl-4-hydroxyindoline, 1-N-(β,γ-dihydroxypropyl)-4-hydroxyindoline, 4-hydroxy-1-N-(β-hydroxyethyl)-5-methylindoline, 4-hydroxy-1-N-(β-hydroxypropyl)-5-methylindoline, 1-N-(β,γ-dihydroxypropyl)-4-hydroxy-5-methylindoline, 4-hydroxy-1-N-(β-hydroxyethyl)-6-methylindoline, 4-hydroxy-1-N-(β-hydroxypropyl)-6-methylindoline, 1-N-(β,γ-dihydroxypropyl)-4-hydroxy-6-methylindoline, 5-benzyl-4-hydroxy-1-N-(β-hydroxyethyl)indoline, 5-benzyl-4-hydroxy-1-N-(β-hydroxypropyl)indoline, 5-benzyl-1-N-(β,γ-dihydroxypropyl)-4-hydroxyindoline, 4-hydroxy-1-N-(β-hydroxyethyl)-5-(β-hydroxyethyl)indoline, 4-hydroxy-5-(β-hydroxyethyl)-1-N-(β-hydroxypropyl)indoline, 1-N-(β,γ-dihydroxypropyl)-4-hydroxy-5-(β-hydroxyethyl)indoline, 4-hydroxy-1-N-(β-hydroxyethyl)-5-(β,γ-dihydroxypropyl)indoline, 4-hydroxy-1-N-(β-hydroxypropyl)-5-(β,γ-dihydroxypropyl)indoline, 1-N-(β,γ-dihydroxypropyl)-4-hydroxy-5-(β,γ-dihydroxypropyl)indoline, 1-N-(γ-dimethylaminopropyl)-4-hydroxyindoline, 1-N-ethylaminoethyl-4-hydroxyindoline, and their acid addition salts.

Preference is more particularly given, among these N-substituted 4-hydroxyindoline derivatives, to:

4-hydroxy-1-N-(β-hydroxyethyl)indoline, 4-hydroxy-1-N-(β-hydroxypropyl)indoline, 1-N-acetyl-4-hydroxyindoline, 1-N-(β,γ-dihydroxypropyl)-4-hydroxyindoline, 4-hydroxy-1-N-(β-hydroxyethyl)-5-methylindoline, 1-N-(γ-dimethylaminopropyl)-4-hydroxyindoline, and their acid addition salts.

The acid addition salts of the compounds of formula (I) which can be used as couplers in the dyeing compositions in accordance with the invention are preferably selected from the hydrochlorides, the hydrobromides, the sulphates and the tartrates.

The N-substituted 4-hydroxyindoline derivative or derivatives of formula (I) preferably represent from 0.0005 to 12% by weight approximately of the total weight of the dyeing composition and more preferably from 0.005 to 6% by weight approximately of this weight.

The nature of the oxidation base or bases which can be used in the dyeing composition according to the invention is not critical. The oxidation base is preferably selected from para-phenylenediamines, bisphenylalkylenediamines, para-aminophenols, ortho-aminophenols, heterocyclic bases and their acid addition salts.

Mention may preferably be made, among the para-phenylenediamines which can be used as oxidation bases in the dyeing composition according to the invention, of the compounds corresponding to the following formula (II) and their acid addition salts:

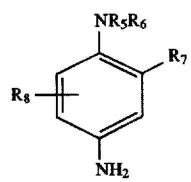

(II)

in which:

$R_5$ represents a hydrogen atom, a $(C_1–C_4)$ alkyl radical, a $(C_1–C_4)$ monohydroxyalkyl radical, a $(C_2–C_4)$ polyhydroxyalkyl radical or a $(C_1–C_4)$alkoxy$(C_1–C_4)$alkyl radical;

$R_6$ represents a hydrogen atom, a $(C_1–C_4)$ alkyl radical, a $(C_1–C_4)$ monohydroxyalkyl radical or a $(C_2–C_4)$ polyhydroxyalkyl radical, $R_7$ represents a hydrogen atom, a halogen atom, such as a chlorine atom, a $(C_1–C_4)$ alkyl radical, a sulpho radical, a carboxyl radical, a $(C_1–C_4)$ monohydroxyalkyl radical or a $(C_1–C_4)$ hydroxyalkoxy radical, $R_8$ represents a hydrogen atom or a $(C_1–C_4)$ alkyl radical.

In the formula (II) above, and when $R_7$ is other than a hydrogen atom, then $R_5$ and $R_6$ preferably represent a hydrogen atom and $R_7$ is preferably identical to $R_8$, and when $R_7$ represents a halogen atom, then $R_5$, $R_6$ and $R_8$ preferably represent a hydrogen atom.

Mention may more preferably be made, among the para-phenylenediamines of formula (II) above, of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-[(β-methoxyethyl)amino]benzene, 2-chloro-para-phenylenediamine and their acid addition salts.

Mention may preferably be made, among the bisphenylalkylenediamines which can be used as oxidation bases in the dyeing composition according to the invention, of the compounds corresponding to the following formula (III) and their acid addition salts:

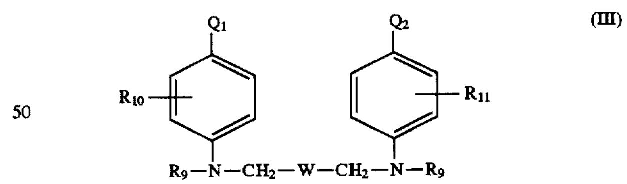

(III)

in which:

$Q_1$ and $Q_2$, which are identical or different, represent a hydroxyl radical or an $NHR_{12}$ radical in which $R_{12}$ represents a hydrogen atom or a $(C_1–C_4)$ alkyl radical, $R_9$ represents a hydrogen atom, a $(C_1–C_4)$ alkyl radical, a $(C_1–C_4)$ monohydroxyalkyl radical, a $(C_2–C_4)$ polyhydroxyalkyl radical or a $(C_1–C_4)$ aminoalkyl radical in which the amino residue can be substituted, $R_{10}$ and $R_{11}$, which are identical or different, represent a hydrogen or halogen atom or a $(C_1–C_4)$ alkyl radical, and W represents a radical selected from the following radicals:

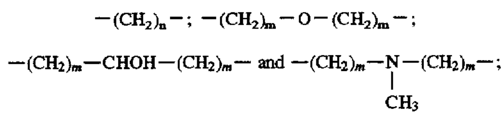

in which n is an integer from 0 to 8 and m is an integer from 0 to 4.

Mention may more preferably be made, among the bisphenylalkylenediamines of formula (III) above, of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bisethyl-N,N'-bis (4'-amino-3'-methylphenyl)ethylenediamine and their acid addition salts.

Among these bisphenylalkylenediamines of formula (III), N,N'-bis(β-hydroxyethyl)-N,N'-bis(4'-aminophenyl)-1,3-diamino-2-propanol or one of its acid addition salts are particularly preferred.

Mention may preferably be made, among the para-aminophenols which can be used as oxidation bases in the dyeing composition according to the invention, of the compounds corresponding to the following formula (IV) and their acid addition salts:

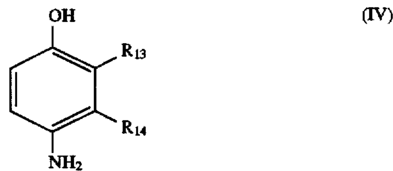

in which:

$R_{13}$ represents a hydrogen atom, a ($C_1$–$C_4$) alkyl radical, a ($C_1$–$C_4$) monohydroxyalkyl radical, a ($C_1$–$C_4$)alkoxy ($C_1$–$C_4$)alkyl radical, a hydroxy($C_1$–$C_4$)alkylamino ($C_1$–$C_4$)alkyl radical or a ($C_1$–$C_4$) aminoalkyl radical;

$R_{14}$ represents a hydrogen or fluorine atom, a $C_1$–$C_4$ alkyl radical, a ($C_1$–$C_4$) monohydroxyalkyl radical, a ($C_2$–$C_4$) polyhydroxyalkyl radical, a ($C_1$–$C_4$) aminoalkyl radical, a ($C_1$–$C_4$) cyanoalkyl radical or a ($C_1$–$C_4$)alkoxy($C_1$–$C_4$)alkyl radical; it being understood that at least one of the $R_{13}$ or $R_{14}$ radicals represents a hydrogen atom.

Mention may more preferably be made, among the para-aminophenols of formula (IV) above, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-(β-hydroxyethyl-aminomethyl)phenol and their acid addition salts.

Mention may preferably be made, among the ortho-aminophenols which can be used as oxidation bases in the dyeing composition according to the invention, of 2-aminophenol, 2-amino-1-hydroxy-5-methylbenzene, 2-amino-1-hydroxy-6-methylbenzene, 5-acetamido-2-aminophenol and their acid addition salts.

Mention may preferably be made, among the heterocyclic bases which can be used as oxidation bases in the dyeing composition according to the invention, of pyridine derivatives, pyrimidine derivatives, pyrazole derivatives and their acid addition salts.

Mention may more preferably be made, among the pyridine derivatives, of the compounds described, for example, in Great Britain Patents GB 1,026,978 and GB 1,153,196, the disclosures of which are hereby incorporated by reference, such as 2,5-diaminopyridine, and their acid addition salts.

Mention may more particularly be made, among the pyrimidine derivatives, of the compounds described, for example, in German Patent DE 2,359,399 or Japanese Patents JP 88-169,571 and JP 91-333,495, the disclosures of which are hereby incorporated by reference, such as 2,4,5,6-tetraaminopyrimidine or 4-hydroxy-2,5,6-triaminopyrimidine, and their acid addition salts.

Mention may more preferably be made, among the pyrazole derivatives, of the compounds described in German Patents DE 3,843,892 and DE 4,133,957, the disclosures of which are hereby incorporated by reference, and PCT Patent Applications WO 94/08969 and WO 94/08970, the disclosures of which are hereby incorporated by reference, such as 4,5-diamino-1-methylpyrazole or 3,4-diaminopyrazole, and their acid addition salts.

According to the invention, the oxidation base or bases preferably represent from 0.0005 to 12% by weight approximately of the total weight of the dyeing composition and still more preferably from 0.005 to 6% by weight approximately of this weight.

The dyeing composition according to the invention can also contain one or a number of additional couplers other than the N-substituted 4-hydroxyindoline derivatives of formula (I) and/or one or a number of direct dyes, so as to vary or enrich in highlights the shades obtained with the oxidation bases.

The additional couplers which can be used in the composition according to the invention can be selected from the couplers conventionally used in oxidation dyeing and among which mention may preferably be made of meta-phenylenediamines, meta-aminophenols, meta-diphenols and heterocyclic couplers, such as, for example, indole derivatives or indoline derivatives, and their acid addition salts.

These couplers are preferably selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline and their acid addition salts.

When they are present, these additional couplers preferably represent from 0.0005 to 5% by weight approximately of the total weight of the dyeing composition and still more preferably from 0.005 to 3% by weight approximately of this weight.

The acid addition salts of the oxidation base or bases and/or of the additional couplers which can be used in the dyeing composition of the invention are preferably selected from the hydrochlorides, the hydrobromides, the sulphates and the tartrates, the lactates and the acetates.

The medium or vehicle, appropriate for the dyeing is generally composed of water or of a mixture of water and of at least one organic solvent for dissolving the compounds which would not be sufficiently soluble in water. Mention may be preferably made, as organic solvent, of, for example, lower $C_1$–$C_4$ alkanols, such as ethanol and isopropanol; glycerol; glycols and glycol ethers such as 2-butoxyethanol, propylene glycol, the monomethyl ether of propylene glycol or the monoethyl ether and the monomethyl ether of diethylene glycol, as well as aromatic alcohols, such as benzyl alcohol or phenoxyethanol, analogous products and their mixtures.

The solvents can be present in proportions preferably of from 1 to 40% by weight approximately with respect to the total weight of the dyeing composition and still more preferably from 5 to 30% by weight approximately.

The pH of the dyeing composition in accordance with the invention is generally from 3 to 12. It can be adjusted to the desired value by means of acidifying or basifying agents commonly used in dyeing keratinous fibres.

Mention may preferably be made, among acidifying agents, by way of example, of inorganic or organic acids, such as hydrochloric acid or orthophosphoric acid, carboxylic acids, such as tartaric acid, citric acid or lactic acid, or sulphonic acids.

Mention may preferably be made, among basifying agents, by way of example, of aqueous ammonia, alkaline carbonates, alkanolamines, such as mono-, di- and triethanolamines, and their derivatives, sodium hydroxide or potassium hydroxide and the compounds of following formula (V):

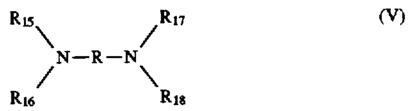

in which R is a propylene residue optionally substituted by a hydroxyl group or a $C_1$–$C_4$ alkyl radical; and $R_{15}$, $R_{16}$, $R_{17}$ and $R_{18}$, which are identical or different, represent a hydrogen atom, a $C_1$–$C_4$ alkyl radical or a $C_1$–$C_4$ hydroxyalkyl radical.

The dyeing composition according to the invention can also contain various adjuvants conventionally used in compositions for dyeing the hair, such as anionic, cationic, nonionic, amphoteric or zwitterionic surface-active agents or their mixtures, anionic, cationic, non-ionic, amphoteric or zwitterionic polymers or their mixtures, inorganic or organic thickening agents, antioxidizing agents, penetrating agents, sequestering agents, fragrances, buffers, dispersing agents, conditioning agents such as, for example, silicones, film-forming agents, preserving agents or opacifying agents.

Of course, the person skilled in the art will take care to choose the possible additional compound or compounds mentioned above so that the advantageous properties intrinsically attached to the dyeing composition according to the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibres and in particular of human hair.

Another subject of the invention is the use of the N-substituted 4-hydroxyindoline derivatives of formula (I) above, as coupler, in combination with at least one oxidation base, for the oxidation dyeing of keratinous fibres and in particular of human keratinous fibres, such as hair.

Another subject of the invention is a process for the oxidation dyeing of keratinous fibres and in particular of human keratinous fibres, such as hair, which makes use of the dyeing composition as defined above.

According to this process, at least one dyeing composition as defined above is applied to the fibres, the colour being developed at acid, neutral or alkaline pH using an oxidizing agent which is added only at the time of use to the dyeing composition or which is present in an oxidizing composition which is applied to the fibers (i) separately from the dyeing composition at the same time that the dyeing composition is applied or (ii) sequentially with the dyeing composition.

According to a particularly preferred embodiment of the dyeing process according to the invention, the dyeing composition described above is mixed, at the time of use, with an oxidizing composition containing, in a medium appropriate for dyeing, at least one oxidizing agent present in an amount sufficient to develop a colouring. The mixture obtained is then applied to the keratinous fibres and left standing for 3 to 50 minutes approximately, preferably 5 to 30 minutes approximately, after which the hair is rinsed, washed with a shampoo, rinsed again and dried.

The oxidizing agent present in the oxidizing composition as defined above can be selected from the oxidizing agents conventionally used for the oxidation dyeing of keratinous fibres and among which mention may preferably be made of hydrogen peroxide, urea hydrogen peroxide, alkali metal bromates, or persalts, such as perborates and persulphates. Hydrogen peroxide is particularly preferred.

The pH of the oxidizing composition containing the oxidizing agent as defined above is such that, after mixing with the dyeing composition, the pH of the resulting composition applied to the keratinous fibres preferably ranges from 3 to 12 approximately and more preferably from 5 to 11. It is adjusted to the desired value by means of acidifying or basifying agents commonly used in dyeing keratinous fibres and as defined above.

The oxidizing composition as defined above can also contain various adjuvants conventionally used in compositions for dyeing hair and as defined above.

The composition which is finally applied to the keratinous fibres can be provided in various forms, such as in the form of liquids, creams or gels, or in any other form appropriate for carrying out dyeing of keratinous fibres and in particular of human hair.

Another subject of the invention is a multi-compartment device or dyeing "kit" or any other multi-compartment packaging system, a first compartment of which contains the dyeing composition as defined above and a second compartment of which contains the oxidizing composition as defined above. These devices can be equipped with a means which makes it possible to deliver the desired mixture onto the hair, such as the devices described in French Patent FR-2,586,913, the disclosure of which is herein incorporated by reference.

Certain compounds of formula (I), used as couplers in the context of the present invention, are novel and, as such, constitute another subject of the invention.

These new N-substituted 4-hydroxyindoline derivatives and their acid addition salts correspond to the following formula (I'):

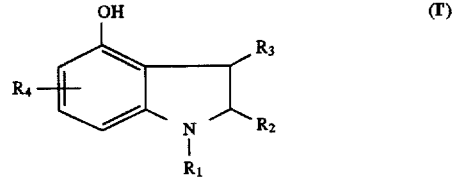

in which:

$R_1$ represents a $(C_1$–$C_4)$ monohydroxyalkyl radical; a $(C_2$–$C_4)$ polyhydroxyalkyl radical; a $(C_1$–$C_4)$alkoxy$(C_1$–$C_4)$alkyl radical; a hydroxy$(C_1$–$C_4)$alkoxy$(C_1$–$C_4)$ alkyl radical; an acetyl or $(C_1$–$C_4)$ aminoalkyl radical; a $(C_1$–$C_4)$ aminoalkyl radical in which the amine is mono- or disubstituted by a $(C_1$–$C_4)$ alkyl group, by an acetyl group, by a $(C_1$–$C_4)$ monohydroxyalkyl group or by a $(C_2$–$C_4)$ polyhydroxyalkyl group; a $(C_1$–$C_4)$ alkylthio$(C_1$–$C_4)$alkyl radical or a monohydroxy $(C_1-C_4)$alkylthio$(C_1-C_4)$alkyl radical; a polyhydroxy $(C_2-C_4)$alkylthio$(C_1-C_4)$alkyl radical; a $(C_1-C_4)$ carboxyalkyl radical; a $(C_1-C_4)$alkoxycarbonyl $(C_1-C_4)$alkyl radical or a acetylamino$(C_1-C_4)$alkyl radical; a $(C_1-C_4)$ cyanoalkyl radical; a $(C_1-C_4)$ trifluoroalkyl radical; a $(C_1-C_4)$ haloalkyl radical; a $(C_1-C_4)$ phosphoalkyl radical or a $(C_1-C_4)$ sulphoalkyl radical;

$R_2$ and $R_3$, which are identical or different, represent a hydrogen or halogen atom; a $(C_1-C_4)$ alkyl radical; a carboxyl radical; a $(C_1-C_4)$alkoxycarbonyl radical or a formyl radical;

$R_4$ represents a hydrogen or halogen atom; a $(C_1-C_4)$ alkyl radical; a $(C_1-C_4)$ alkoxy radical; an acetylamino radical; a $(C_1-C_5)$ monohydroxyalkyl radical; a $(C_2-C_4)$ polyhydroxyalkyl radical; a $(C_1-C_4)$alkoxy $(C_1-C_4)$alkyl radical; a thiophene radical, a furan radical; a phenyl radical; a $(C_1-C_4)$ aralkyl radical; a phenyl or $(C_1-C_4)$ aralkyl radical substituted by a halogen atom, a $(C_1-C_4)$ alkyl, a trifluoromethyl, a $(C_1-C_4)$ alkoxy or an amino or by an amino mono- or disubstituted by a $(C_1-C_4)$ alkyl radical; a $(C_1-C_4)$ alkylamino$(C_1-C_4)$alkyl radical or a di$(C_1-C_4)$ alkylamino$(C_1-C_4)$alkyl radical;

it being understood that:

when $R_2$, $R_3$ and $R_4$ simultaneously represent a hydrogen atom, then $R_1$ cannot represent a methoxycarbonylpropyl radical.

Preferably, according to the present invention, the $R_1$ substituent is chosen from the $(C_1-C_4)$ monohydroxyalkyl radicals and the $(C_2-C_4)$ polyhydroxyalkyl radicals.

Mention may preferably be made among the new N-substituted 4-hydroxyindoline derivatives of formula (I'), of:

4-hydroxy-1-N-(β-hydroxyethyl)indoline, 4-hydroxy-1-N-(β-hydroxypropyl)indoline, 1-N-acetyl-4-hydroxyindoline, 1-N-(β,γ-dihydroxypropyl)-4-hydroxyindoline, 4-hydroxy-1-N-(β-hydroxyethyl)-5-methylindoline, 4-hydroxy-1-N-(β-hydroxypropyl)-5-methylindoline, 1-N-(β,γ-dihydroxypropyl)-4-hydroxy-5-methylindoline, 4-hydroxy-1-N-(β-hydroxyethyl)-6-methylindoline, 4-hydroxy-1-N-(β-hydroxypropyl)-6-methylindoline, 1-N-(β,γ-dihydroxypropyl)-4-hydroxy-6-methylindoline, 5-benzyl-4-hydroxy-1-N-(β-hydroxyethyl)indoline, 5-benzyl-4-hydroxy-1-N-(β-hydroxypropyl)indoline, 5-benzyl-1-N-(β,γ-dihydroxypropyl)-4-hydroxyindoline, 4-hydroxy-1-N-(β-hydroxyethyl)-5-(β-hydroxyethyl) indoline, 4-hydroxy-5-(β-hydroxyethyl)-1-N-(β-hydroxypropyl) indoline, 1-N-(β,γ-dihydroxypropyl)-4-hydroxy-5-(β-hydroxyethyl)indoline, 4-hydroxy-1-N-(β-hydroxyethyl)-5-(β,γ-dihydroxypropyl)indoline, 4-hydroxy-1-N-(β-hydroxypropyl)-5-(β,γ-dihydroxypropyl)indoline, 1-N-(β,γ-dihydroxypropyl)-4-hydroxy-5-(β,γ-dihydroxypropyl)indoline, 1-N-(γ-dimethylaminopropyl)-4-hydroxyindoline, 1-N-ethylaminoethyl-4-hydroxyindoline, and their acid addition salts.

Preference is more particularly given, among these new N-substituted 4-hydroxyindoline derivatives of formula (I'), to:

4-hydroxy-1-N-(β-hydroxyethyl)indoline, 4-hydroxy-1-N-(β-hydroxypropyl)indoline, 1-N-acetyl-4-hydroxyindoline, 1-N-(β,γ-dihydroxypropyl)-4-hydroxyindoline, 4-hydroxy-1-N-(β-hydroxyethyl)-5-methylindoline, 1-N-(γ-dimethylaminopropyl)-4-hydroxyindoline, and their acid addition salts.

Another subject of the invention is a process (main process) for the preparation of the compounds of formula (I'), corresponding to the following synthetic scheme:

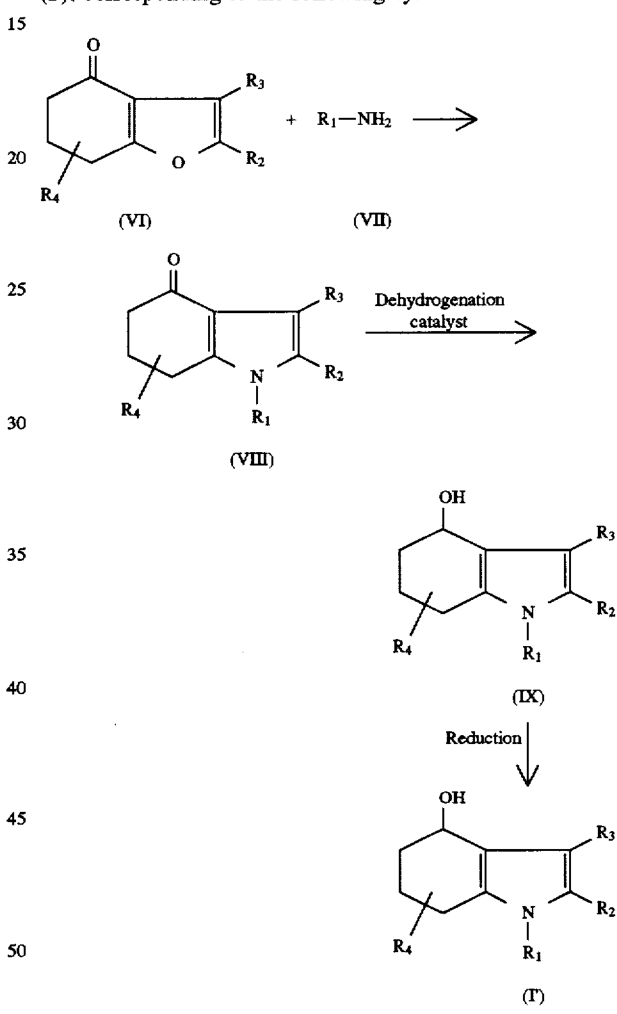

In a first stage, 4-oxo-4,5,6,7-tetrahydrobenzofuran of formula (VI), in which the $R_2$, $R_3$ and $R_4$ radicals have the same meaning as in the formula (I') defined above, is reacted with a substituted amine of formula (VII), in which the $R_1$ radical has the same meaning as in the formula (I') defined above, in a solvent medium in which the temperature preferably ranges from 80° to 160° C., to result in a 4-oxo-4,5,6,7-tetrahydroindole derivative of formula (VIII), in which the $R_1$, $R_2$, $R_3$ and $R_4$ radicals have the same meaning as in the formula (I') defined above. In a second stage, the compound of formula (VIII) is aromatized by catalytic dehydrogenation in solvent medium, at a temperature generally ranging from 150° to 220° C. and preferably ranging from 160° to 170° C., to result in a compound of formula (IX), in which the $R_1$, $R_2$, $R_3$ and $R_4$ radicals have the same meaning as in the formula (I') defined above. Finally, in a third stage, in acid medium and at a temperature generally of from 10° to 40° C., the double bond of the pyrrole ring of the compound of formula (IX) is reduced using chemical reducing agents, to result in a compound of formula (I') defined above.

Mention may more preferably be made, among the solvents used during the first stage, of lower alcohols, such as ethanol, n-propanol, 1-butanol, 2-butanol, 2-methyl-1-butanol, 3-methyl-1-butanol, 2-methyl-1-propanol, n-pentanol, 2-pentanol, 3-methyl-3-pentanol, 4-methyl-2-pentanol or alternatively 2-ethyl-1-butanol.

According to the process of the invention, any appropriate dehydrogenation catalyst may be used. For example, a metal selected from manganese, platinum, palladium, rhodium, nickel and ruthenium, their oxides and the combinations of these substances may be used as the dehydrogenation catalyst.

The preferred dehydrogenation catalysts are palladium or platinum. The catalyst can be deposited on an inert support in a known way. Mention may preferably be made, among these inert supports, of, for example, neutral wood charcoal, neutral charcoal, neutral alumina, zeolites, clays, and the like. Neutral charcoal is preferably used.

The dehydrogenation catalysts are generally present in an amount of from 0.2 to 5% by weight of equivalent metal with respect to the weight of the compound of formula (VIII) to be reacted.

The solvents used during the second stage are preferably selected from solvents with a boiling point greater than 150° C., such as, for example, diglyme, the boiling point (B.P.) of which is approximately 162° C., and diisobutyl ketone (B.P. of approximately 169° C.).

The reaction of reducing the double bond of the pyrrole ring of the compound of formula (IX) (third stage) is well known to the person skilled in the art and is described, for example, in the monograph by R. T. Brown, J. A. Joule and P. G. Sammes, "Comprehensive Organic Chemistry", Vol. 4, p. 443, Pergamon Press, 1979, the disclosure of which is incorporated herein by reference.

The solvents used during this third stage are preferably selected from carboxylic acids, such as acetic acid, trifluoroacetic acid and trichloroacetic acid.

According to a first alternative form of this main process and when, in the formula (VI), the $R_4$ radical is a hydrogen atom, it is possible to introduce a $R'_4$ radical, other than a hydrogen atom, into the compounds of formula (VIII) at the 5-position by an aldol reaction in basic medium. This first alternative form corresponds to the following synthetic scheme:

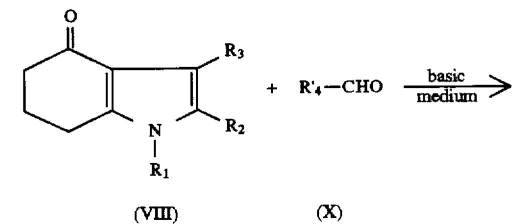

-continued

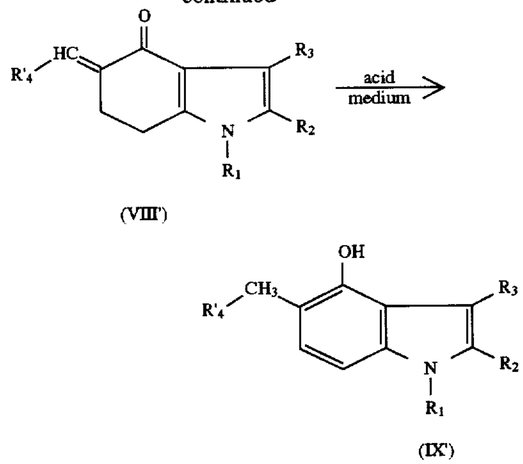

comprising the reaction of a compound of formula (VIII) and an aldehyde of formula (X), in which the $R'_4$ radical represents a $(C_1-C_3)$ alkyl radical, a $(C_1-C_4)$ monohydroxyalkyl radical, a $(C_2-C_3)$ polyhydroxyalkyl radical, a $(C_1-C_3)$ alkoxyalkyl radical, a $(C_1-C_4)$alkylamino$(C_1-C_3)$alkyl radical or a di$(C_1-C_4)$alkylamino$(C_1-C_3)$alkyl radical, in basic medium, to obtain a compound of formula (VIII'), in which the $R'_4$ radical has the same meaning as in the formula (X). The compound of formula (VIII) is then isomerized in acid medium according to conventional isomerization conditions, to result in a compound of formula (IX') in which the $R_1$, $R_2$ and $R_3$ radicals have the same meanings as in the formula (I') and the $R'_4$ radical has the same meaning as in the formula (X). The compound of formula (IX') is then reduced according to the method described for the main process, to result in a compound of formula (I').

The aldol reaction is well known to the person skilled in the art and is described, for example, in European Patent Application EP-A-0,377,450, the disclosure of which is incorporated herein by reference.

According to a second alternative form of this main process, it is also possible to functionalize the benzene part of the compounds of formula (IX) obtained from a compound of formula (VIII) in which $R_4$ represents a hydrogen atom, in order to introduce an $R_4$ radical other than a hydrogen atom. This second alternative form corresponds to the following synthetic scheme:

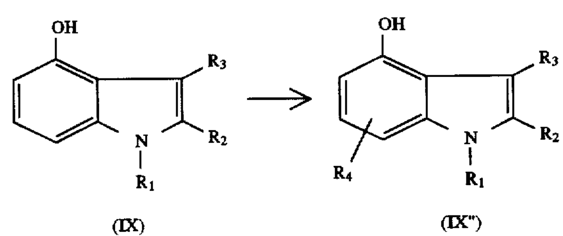

The compound of formula (IX") is then reduced according to the method described in the third stage of the main process, to result in a compound of formula (I').

This second alternative form makes it possible in particular to introduce:

either an $R_4$ substituent of di$(C_1-C_4)$alkylaminomethyl type, at the 5-position, by a Mannich reaction, as described, for example, in the article by F. Troxler et al., Helv. Chim. Acta, 51, (6), 1968, the disclosure of which is incorporated herein by reference;

or an $R_4$ substituent of acetylamino type by a nitration reaction followed by a reduction reaction and by an acetylation, by conventional methods well known to the person skilled in the art;

or alternatively an $R_4$ substituent of halogen type, by a conventional halogenation reaction, when the $R_2$ and $R_3$ radicals are both other than a hydrogen atom.

This listing is not, of course, limiting of the type of $R_4$ groups which can be introduced directly into the compounds of formula (IX).

The following examples are intended to illustrate the invention without limiting the scope thereof in any way.

PREPARATION EXAMPLES

PREPARATION EXAMPLE 1

Synthesis of 4-hydroxy-1-N-(β-hydroxypropyl) indoline

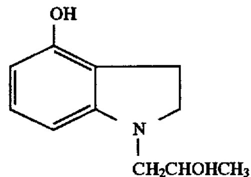

a) Preparation of 4-oxo-4,5,6,7-tetrahydro-1-N-(β-hydroxypropyl)indole 7.2 g of β-hydroxypropylamine were added to a solution of 13.6 g of 4-oxo-4,5,6,7-tetrahydrobenzofuran in 200 cm$^3$ of ethanol. The solution was brought to 150° C. for 4 hours. The ethanol was then evaporated under vacuum. 18 g of an oil were collected, which oil was used in the following stage.

b) Preparation of 4-hydroxy-1-N-(β-hydroxypropyl)indole 10 g of 5% by weight palladium-on-charcoal, containing 50% of water, were added to a solution of 19.3 g of 4-oxo-4,5,6,7-tetrahydro-1-N-(β-hydroxypropyl)indole, obtained in the preceding stage, in 300 cm$^3$ of diglyme. The temperature of the reaction mixture was brought to the reflux temperature of the diglyme for 5 hours, after removal of the water by azeotropic distillation. The catalyst was then filtered off on Celite and the diglyme was then evaporated. 17 g of crude product were obtained. After chromatography on silica gel (heptane/ethyl acetate=1/4), 15 g of a viscous product were obtained, which product crystallized on addition of 15 cm$^3$ of dichloromethane.

After filtering, washing with petroleum ether and drying under vacuum and over phosphorus pentoxide, 10 g of 4-hydroxy-1-N-(β-hydroxypropyl)indole were recovered, the melting point of which was between 93° and 95° C.

c) Preparation of 4-hydroxy-1-N-(β-hydroxypropyl)indoline 1.4 g of sodium cyanoborohydride were added to a solution of 7 g of 4-hydroxy-1-N-(β-hydroxypropyl)indole, obtained in the preceding stage, in 40 cm$^3$ of acetic acid, the temperature being maintained below 30° C. After stirring for 30 minutes, the reaction mixture was poured onto 200 g of ice-cold water and the pH was neutralized to 7.5 by addition of 30% aqueous ammonia. The precipitate obtained was filtered off and dried. 4 g of the expected product were obtained, the melting point of which was between 130° and 131° C. and the elemental analysis of which, calculated for $C_{11}H_{15}NO_2$, was as follows:

| | % | | | |
|---|---|---|---|---|
| | C | H | N | O |
| Calculated | 68.37 | 7.82 | 7.25 | 16.56 |
| Found | 68.37 | 7.80 | 7.29 | 16.52 |

PREPARATION EXAMPLE 2

Synthesis of 4-hydroxy-1-N-(β-hydroxyethyl) indoline

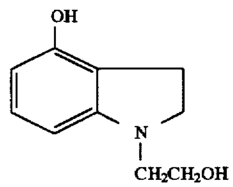

a) Preparation of 4-oxo-4,5,6,7-tetrahydro-1-N-(β-hydroxyethyl)indole 80 g of ethanolamine were added to a solution of 136 g of 4-oxo-4,5,6,7-tetrahydrobenzofuran in 250 cm$^3$ of ethanol. The solution was brought to 130° C. for 6 hours. After having allowed the reaction mixture to return to room temperature with stirring, the latter was run onto a mixture of 800 cm$^3$ of isopropyl ether and 200 cm$^3$ of petroleum ether. A product crystallized with stirring and was then filtered off, washed with petroleum ether and dried under vacuum over phosphorus pentoxide. 160 g of the expected product were collected, which product was recrystallized from 240 cm$^3$ of isopropanol. 150 g of the expected product were obtained, the melting point of which was between 96° and 97° C.

b) Preparation of 4-hydroxy-1-N-(β-hydroxyethyl)indole 15 g of 5% by weight palladium-on-charcoal, containing 50% of water, were added to a solution of 25 g of 4-oxo-4,5,6,7-tetrahydro-1-N-(β-hydroxyethyl)indole, obtained in the preceding stage, in 300 cm$^3$ of diglyme. The temperature of the mixture was brought to and maintained at 162° C. for 10 hours. The mixture was then allowed to return to a temperature of 40° C. and the catalyst was then filtered off. The solvents were then removed under vacuum until 21.4 g of crude product were obtained, which were taken up in a mixture of 30 cm$^3$ of dichloromethane and 200 cm$^3$ of petroleum ether. The crystals obtained were filtered off, washed with petroleum ether and then dried under vacuum over phosphorus pentoxide. 11 g of 4-hydroxy-1-N-(β-hydroxyethyl)indole were obtained, the melting point of which was 109° C.

c) Preparation of 4-hydroxy-1-N-(β-hydroxyethyl)indoline 1.9 g of sodium cyanoborohydride were added to a solution of 8.85 g of 4-hydroxy-1-N-(β-hydroxyethyl) indole, obtained in the preceding stage, in 40 cm$^3$ of acetic acid, the temperature being maintained below 30° C. After stirring for 30 minutes, the reaction mixture was poured onto 200 g of ice-cold water and the pH was neutralized to 7.5 by addition of 30% aqueous ammonia. The precipitate obtained was filtered off and dried. 7.75 g of 4-hydroxy-1-N-(β-hydroxyethyl)indoline were obtained, the melting point of which was 108° C. $^{13}C$ and proton nuclear magnetic resonance (N.M.R.) analysis of the product obtained was found to be in accordance with the expected product.

PREPARATION EXAMPLE 3

Synthesis of the hydrochloride of 4-hydroxy-1-N-(β,γ-dihydroxypropyl)indoline

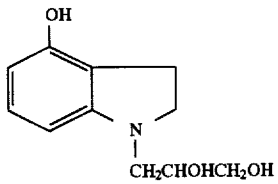

a) Preparation of 4-oxo-4,5,6,7-tetrahydro-1-N-(β,γ-dihydroxypropyl)indole 9.4 g of 2,3-dihydroxypropylamine were added to a solution of 13.6 g of 4-oxo-4,5,6,7-tetrahydrobenzofuran in 200 $cm^3$ of ethanol. The reaction mixture was heated at 150° C. for 9 hours. After evaporation of the solvent and purification of the crude product on silica gel (ethyl acetate/methanol=9/1), 11.2 g of 4-oxo-4,5,6,7-tetrahydro-1-N-(β,γ-dihydroxypropyl)indole were collected in the form of an oil.

b) Preparation of 4-hydroxy-1-N-(β,γ-dihydroxypropyl)indole 3.8 g of 5% by weight palladium-on-charcoal, containing 50% of water, were introduced into a solution of 9.4 g of 4-oxo-4,5,6,7-tetrahydro-1-N-(β,γ-dihydroxypropyl)indole, obtained in the preceding stage, in 50 $cm^3$ of diglyme. The temperature of the reaction mixture was brought to the reflux temperature of the diglyme and the water was azeotropically distilled. After reacting for 23 hours, the catalyst was filtered off on Celite and the diglyme was then evaporated under vacuum. The crude product obtained was chromatographed on silica gel (ethyl acetate/heptane=9/1). 4.2 g of 4-hydroxy-1-N-(β,γ-dihydroxypropyl)indole were obtained in the form of a very viscous oil.

c) Preparation of the hydrochloride of 4-hydroxy-1-N-(β,γ-dihydroxypropyl)indoline 0.7 g of sodium cyanoborohydride was added to a solution of 4 g of 4-hydroxy-1-N-(β,γ-dihydroxypropyl)indole, obtained in the preceding stage, in 40 $cm^3$ of acetic acid, the temperature being maintained below 30° C. After stirring for 30 minutes, the reaction mixture was poured onto 200 g of ice-cold water and the pH was neutralized to 7.5 by addition of 30% aqueous ammonia. The precipitate obtained was filtered off and dried. After treating the precipitate with a 5.5M ethanolic hydrochloric acid solution, 3.4 g of the expected product were obtained, the elemental analysis of which, calculated for $C_{11}H_{15}NO_3HCl$, was as follows:

| | % | | | | |
|---|---|---|---|---|---|
| | C | H | N | O | Cl |
| Calculated | 53.77 | 6.56 | 5.7 | 19.53 | 14.43 |
| Found | 52.91 | 6.53 | 5.68 | 18.96 | 14.82 |

FORMULATION EXAMPLES FORMULATION EXAMPLES 1 (inventive) and 2 (comparitive) The following dyeing compositions were prepared (contents in grams):

| Compositions | 1 | 2(*) |
|---|---|---|
| 4-Hydroxy-1-N-(β-hydroxyethyl)indoline | 0.895 | |
| 4-Hydroxy-1-N-methylindoline | | 0.745 |
| para-Phenylenediamine | 0.540 | 0.540 |
| Common dyeing vehicle | (**) | (**) |
| Demineralized water q.s. for | 100 g | 100 g |

(*)Example not forming part of the invention
(**)Common dyeing vehicle:

| | |
|---|---|
| Oleyl alcohol polyglycerolated with 2 mol of glycerol | 4.0 g |
| Oleyl alcohol polyglycerolated with 4 mol of glycerol containing 78% of active materials (A.M.) | 5.69 g A.M. |
| Oleic acid | 3.0 g |
| Oleamine containing 2 mol of ethylene oxide, sold under the trade name Ethomeen O12 by the company Akzo | 7.0 g |
| Diethylaminopropyl laurylamino-succinamate, sodium salt, containing 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulphite as an aqueous solution containing 35% of A.M. | 0.455 g A.M. |
| Ammonium acetate | 0.8 g |
| Antioxidant, sequestrant | q.s. |
| Fragrance, preservative | q.s. |
| Aqueous ammonia containing 20% of $NH_3$ | 10.0 g |

At the time of use, each dyeing composition 1 and 2 was mixed with an equal weight of 20 volume hydrogen peroxide (6% by weight).

Each mixture obtained was applied for 30 minutes to locks of permed grey hair containing 90% of white hairs. After rinsing, washing with a standard shampoo and drying, the locks were dyed in the shades which appear in Table I below:

| Example | 1 | 2(*) |
|---|---|---|
| Shade obtained | Iridescent mahogany brown | Coppery mahogany brown |

(*)Example not forming part of the invention

The locks, thus dyed, were then subjected to a test of resistance to light (Xenotest).

To do this, the locks of dyed hair were attached to a support (cardboard or plastic). These supports were arranged on sample holders which were made to rotate around a Xenon lamp for a period of 40 hours at a relative humidity level of 25±5% and at a temperature of 42.5°±2.5° C.

The colour of the locks was evaluated in the Munsell system, before and after the test of resistance to light, by means of a Minolta CM 2002 calorimeter.

According to the Munsell notation, a colour is defined by the expression HV/C in which the three parameters respectively denote the shade or Hue (H), the intensity or Value (V) and the purity or Chromaticity (C); the oblique stroke in this expression is simply a convention and does not indicate a ratio.

The difference in colour of each lock before and after the test of resistance to light reflects the deterioration in the colouring due to the effect of light and was calculated by applying the Nickerson formula: $\Delta E=0.4Co\Delta H+6\Delta V+3\Delta C$, as described, for example, in "Couleur, Industrie et Technique [Colour, Industry and Technology]", pages 14–17, Vol. No. 5, 1978, the disclosure of which is herein incorporated by reference.

In this formula, ΔE represents the difference in colour between two locks, ΔH, ΔV and ΔC represent the variation in absolute value of the parameters H, V and C, and Co represents the purity of the lock with respect to which it is desired to evaluate the difference in colour (purity of the lock before the test).

The results are given in Table II below:

| EXAMPLE | Colour before the test | Colour after the test | Deterioration in the colouring ΔH | ΔV | ΔC | ΔE |
|---|---|---|---|---|---|---|
| 1 | 3.1 YR 2.4/1.7 | 4.0 YR 2.6/1.8 | 0.9 | 0.2 | 0.1 | 2.1 |
| 2(*) | 4.2 YR 2.5/1.9 | 5.5 YR 3.1/2.3 | 1.3 | 0.6 | 0.4 | 5.8 |

(*)Example not forming part of the invention

It was found that the colouring obtained with the dyeing composition of Example 1 according to the invention (containing 4-hydroxy-1-N-(β-hydroxyethyl)indoline) is much more resistant to the effect of light than the colouring obtained with the dyeing composition of Example 2, which does not form part of the invention because it contains 4-hydroxy-1-N-methylindoline, a compound which does not correspond to the formula (I) defined above and which corresponds to a compound of the prior art as described in French Patent Application FR-A-2,008,797.

What is claimed is:

1. A composition for dyeing keratinous fibres comprising, in a medium appropriate for dyeing, as a coupler, at least one of a N-substituted 4-hydroxyindoline derivative of formula (I) and its acid addition salts:

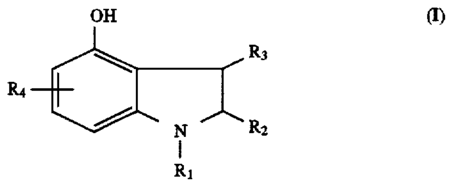

wherein:

$R_1$ represents a $(C_1–C_4)$ monohydroxyalkyl radical; a $(C_2–C_4)$ polyhydroxyalkyl radical; a $(C_1–C_4)$alkoxy$(C_1–C_4)$alkyl radical; a hydroxy$(C_1–C_4)$alkoxy$(C_1–C_4)$alkyl radical; an acetyl radical; a $(C_1–C_4)$ aminoalkyl radical; a $(C_1–C_4)$ aminoalkyl radical in which the amine is mono- or disubstituted by a $(C_1–C_4)$ alkyl group, by an acetyl group, by a $(C_1–C_4)$ monohydroxyalkyl group or by a $(C_2–C_4)$ polyhydroxyalkyl group; a $(C_1–C_4)$alkylthio$(C_1–C_4)$alkyl radical or a monohydroxy$(C_1–C_4)$alkylthio$(C_1–C_4)$alkyl radical; a polyhydroxy$(C_2–C_4)$alkylthio$(C_1–C_4)$alkyl radical; a $(C_1–C_4)$ carboxyalkyl radical; a $(C_1–C_4)$ alkoxycarbonyl$(C_1–C_4)$alkyl radical or a acetylamino $(C_1–C_4)$alkyl radical; a $(C_1–C_4)$ cyanoalkyl radical; a $(C_1–C_4)$ trifluoroalkyl radical; a $(C_1–C_4)$ haloalkyl radical; a $(C_1–C_4)$ phosphoalkyl radical or a $(C_1–C_4)$ sulphoalkyl radical;

$R_2$ and $R_3$, which are identical or different, represent a hydrogen or halogen atom; a $(C_1–C_4)$ alkyl radical; a carboxyl radical; a $(C_1–C_4)$alkoxycarbonyl radical or a formyl radical;

$R_4$ represents a hydrogen or halogen atom; a $(C_1–C_4)$ alkyl radical; a $(C_1–C_4)$ alkoxy radical; an acetylamino radical; a $(C_1–C_5)$ monohydroxyalkyl radical; a $(C_2–C_4)$ polyhydroxyalkyl radical; a $(C_1–C_4)$alkoxy $(C_1–C_4)$alkyl radical; a thiophene radical; a furan radical; a phenyl radical; a $(C_1–C_4)$ aralkyl radical; a phenyl or $(C_1–C_4)$ aralkyl radical substituted by a halogen atom, a $(C_1–C_4)$ alkyl, a trifluoromethyl, a $(C_1–C_4)$ alkoxy or an amino or by an amino mono- or disubstituted by a $(C_1–C_4)$ alkyl radical; a $(C_1–C_4)$ alkylamino$(C_1–C_4)$alkyl radical or a di$(C_1–C_4)$ alkylamino$(C_1–C_4)$alkyl radical; wherein said $(C_1–C_4)$ alkyl and $(C_1–C_4)$ alkoxy groups are linear or branched, and at least one oxidation base.

2. A composition according to claim 1 wherein said halogen atom is selected from chlorine, bromine, iodine or fluorine.

3. A composition according to claim 1, wherein $R_1$ is selected from $(C_1–C_4)$ monohydroxyalkyl radicals or $(C_2–C_4)$ polyhydroxyalkyl radicals.

4. A composition according to claim 1, wherein said N-substituted 4-hydroxyindoline derivative of formula (I) is selected from:

4-hydroxy-1-N-(β-hydroxyethyl)indoline,
4-hydroxy-1-N-(β-hydroxypropyl)indoline,
1-N-acetyl-4-hydroxyindoline,
1-N-(β,γ-dihydroxypropyl)-4-hydroxyindoline,
4-hydroxy-1-N-(β-hydroxyethyl)-5-methylindoline,
4-hydroxy-1-N-(β-hydroxypropyl)-5-methylindoline,
1-N-(β,γ-dihydroxypropyl)-4-hydroxy-5-methylindoline,
4-hydroxy-1-N-(β-hydroxyethyl)-6-methylindoline,
4-hydroxy-1-N-(β-hydroxypropyl)-6-methylindoline,
1-N-(β,γ-dihydroxypropyl)-4-hydroxy-6-methylindoline,
5-benzyl-4-hydroxy-1-N-(β-hydroxyethyl)indoline,
5-benzyl-4-hydroxy-1-N-(β-hydroxypropyl)indoline,
5-benzyl-1-N-(β,γ-dihydroxypropyl)-4-hydroxyindoline,
4-hydroxy-1-N-(β-hydroxyethyl)-5-(β-hydroxyethyl) indoline,
4-hydroxy-5-(β-hydroxyethyl)-1-N-(β-hydroxypropyl) indoline,
1-N-(β,γ-dihydroxypropyl)-4-hydroxy-5-(β-hydroxyethyl)indoline,
4-hydroxy-1-N-(β-hydroxyethyl)-5-(β,γ-dihydroxypropyl)indoline,
4-hydroxy-1-N-(β-hydroxypropyl)-5-(β,γ-dihydroxypropyl)indoline,
1-N-(β,γ-dihydroxypropyl)-4-hydroxy-5-(β,γ-dihydroxypropyl)indoline,
1-N-(γ-dimethylaminopropyl)-4-hydroxyindoline,
1-N-ethylaminoethyl-4-hydroxyindoline, or the acid addition salts thereof.

5. A composition according to claim 4, wherein said derivative of formula (I) is selected from:

4-hydroxy-1-N-(β-hydroxyethyl)indoline,
4-hydroxy-1-N-(β-hydroxypropyl)indoline,
1-N-acetyl-4-hydroxyindoline,
1-N-(β,γ-dihydroxypropyl)-4-hydroxyindoline, 4-hydroxy-1-N-(β-hydroxyethyl)-5-methylindoline, 1-N-(γ-dimethylaminopropyl)-4-hydroxyindoline, or the acid addition salts thereof.

6. A composition according to claim 1, wherein said acid addition salts of said derivative of formula (I) are selected from the hydrochlorides, the hydrobromides, the sulphates or the tartrates.

7. A composition according to claim 1, wherein said derivative of formula (I) represents from 0.0005 to 12% by weight of the total weight of the dyeing composition.

8. A composition according to claim 7, wherein said derivative of formula (I) represents from 0.005 to 6% by weight of the total weight of the dyeing composition.

9. A composition according to claim 1, wherein said at least one oxidation base is selected from para-phenylenediamines, bisphenylalkylenediamines, para-aminophenols, orthoaminophenols, heterocyclic bases or the acid addition salts thereof.

10. A composition according to claim 1, wherein said at least one oxidation base represents from 0.0005 to 12% by weight approximately of the total weight of the dyeing composition.

11. A composition according to claim 10, wherein said at least one oxidation base represents from 0.005 to 6% by weight approximately of the total weight of the dyeing composition.

12. A composition according to claim 1, additionally containing at least one of one or more additional couplers other than the N-substituted 4-hydroxyindoline derivatives of formula (I) and at least one direct dye.

13. A composition according to claim 1, wherein said medium appropriate for dyeing comprises water or a mixture of water and at least one organic solvent selected from lower $C_1$–$C_4$ alkanols, glycerol, glycols and glycol ethers, aromatic alcohols, or mixtures thereof.

14. A composition according to claim 1, wherein said composition has a pH of from 3 to 12.

15. A composition according to claim 1, wherein said composition is in the form of a liquid, cream, or gel or in any other form appropriate for carrying out dyeing of keratinous fibres.

16. A process for the oxidation dyeing of keratinous fibers, said process comprising the step of applying to said keratinous fibers a composition comprising, as a coupler, said N-substituted 4-hydroxyindoline derivative of formula (I) as defined in claim 1 and at least one oxidation base.

17. A process according to claim 16, wherein said keratinous fibers are human keratinous fibers.

18. A process according to claim 17, wherein said human keratinous fibers are hair.

19. A process for the oxidation dyeing of keratinous fibres, said process comprising the following steps:

applying to said fibers at least one dyeing composition as defined in claim 1, and developing the color at acid, neutral or alkaline pH by application of an effective amount of an oxidizing agent, wherein said oxidizing agent is added to said at least one dyeing composition only at the time of application or is present in an oxidizing composition which is applied:

(i) separately from said dyeing composition at the same time that said dyeing composition is applied to said fibers or (ii) sequentially with said dyeing composition.

20. A process according to claim 19, wherein said keratinous fibers are human keratinous fibers.

21. A process according to claim 20, wherein said human keratinous fibers are hair.

22. A process according to claim 19, further comprising the step of leaving said at least one dyeing composition on said keratinous fibers for approximately 3 to 50 minutes.

23. A process according to claim 22, further comprising the steps of:

rinsing said keratinous fibers after said at least one dyeing composition has been left on them for approximately 3 to 50 minutes;

washing said keratinous fibers;

rinsing said washed keratinous fibers; and drying said keratinous fibers.

24. A process according to claim 19, wherein said oxidizing agent is selected from hydrogen peroxide, urea hydrogen peroxide, alkali metal bromates, or persalts.

25. A process according to claim 24, wherein said persalts are selected from perborates or persulphates.

26. A multi-compartment dyeing device comprising a first compartment containing a dyeing composition as defined in claim 1 and a second compartment containing an oxidizing composition.

* * * * *